United States Patent [19]

Noguchi et al.

[11] Patent Number: 4,952,058
[45] Date of Patent: Aug. 28, 1990

[54] METHOD AND APPARATUS FOR DETECTING ABNORMAL PATTERNS

[75] Inventors: Minori Noguchi; Hiroaki Shishido; Mitsuyoshi Koizumi, all of Yokohama, Japan

[73] Assignee: Hitach, Ltd., Tokyo, Japan

[21] Appl. No.: 184,787

[22] Filed: Apr. 22, 1988

[30] Foreign Application Priority Data

Apr. 27, 1987 [JP] Japan ................................. 62-101745
Jun. 19, 1987 [JP] Japan ................................. 62-151121

[51] Int. Cl.⁵ .......................................... G01N 21/88
[52] U.S. Cl. ................................... 356/237; 356/394; 356/446
[58] Field of Search ................. 356/237, 394, 239, 446

[56] References Cited

U.S. PATENT DOCUMENTS

4,330,205  5/1982  Murakami et al. .................. 356/237
4,601,577  7/1986  Gotou et al. ......................... 356/237
4,681,442  7/1987  Wagner ................................ 356/237

Primary Examiner—Vincent P. McGraw
Assistant Examiner—S. A. Turner
Attorney, Agent, or Firm—Antonelli, Terry, Stout & Kraus

[57] ABSTRACT

A system for detecting abnormal patterns in a surface pattern on the surface of a sample wherein, when the abnormal pattern has a portion smaller than the surface pattern, the light for illuminating the sample is stopped down to an opening so that the abnormal pattern can be distinguished over the surface pattern, the surface pattern is limited to a predetermined opening by the illumination light to form an image on a detector, and the surface pattern detected by the detector is processed to detect the abnormal pattern in the surface pattern. Further, the plurality of light rays having good directivity are illuminated onto a point on the surface of the sample from dissimilar directions maintaining a predetermined angle of incidence, the detect signals are separated to be corresponded to said light rays, and the above processing is carried out to enhance the precision of detection.

24 Claims, 7 Drawing Sheets

METHOD AND APPARATUS FOR DETECTING ABNORMAL PATTERNS

BACKGROUND OF THE INVENTION

1. Field of the Invention

The present invention relates to a method and an apparatus for detecting patterns such as reticles and masks used for the fabrication of semiconductor devices having a high degree of integration such as LSI's. More specifically, the invention relates to a method and an apparatus for detecting abnormal patterns suited for discriminating and detecting tiny foreign matter (inclusive of pattern defects) adhered on the reticles and masks from the pattern edges.

2. Description of the Prior Art

The prior art will now be described with reference to the case of detecting tiny abnormal patterns on the reticles in the process for fabricating LSI's which is a representative technology to which the present invention is adapted.

In the exposure step used for the fabrication of LSI's, a chrome pattern on a thick plate called a reticle is printed by baking onto a semiconductor wafer. When foreign matter and defects exist on the reticle in this step, the pattern is not correctly printed onto the semiconductor wafer, and all of the LSI chips become defective. It is therefore essential to inspect for foreign matter and defects prior to the exposure from the standpoint of controlling the quality of reticles.

In recent years, smaller foreign matter is imposing another problem as the wiring patterns become more fine accompanying the increase in the integration degree of LSI's. In preparing the reticles, furthermore, the resist remains, chromium or chromium oxide for pattern formation remains after etching, and impurities dissolved in the reticle wash liquid coagulate at the time of wash and dry, imposing a problem of formation of foreign contaminant film which is on the increase.

A conventional apparatus for inspecting foreign matter and defects consists, as disclosed, for example, in Japanese Patent Laid-Open No. 65428 /1984, of means for illuminating a substrate by a laser beam from a tilted direction, a first lens which is provided above the substrate so that an illuminating point of the laser beam and a plane of focal point are nearly in agreement with each other, and which focuses the scattering light of a laser beam, a shutter which is provided on a Fourier transformed plane of the first lens and which shuts off the regularly scattered light from the substrate pattern, a second lens which subjects the scattered light from foreign matter obtained through the shutter to the inverse Fourier transformation, a slit which is provided at the imaging point of the second lens to shut off the scattered light from the areas other than the laser beam illuminating point on the substrate, and a light receiver which receives the scattering light from foreign matter that has passed through the slit.

According to the above apparatus, attention is given to the fact that a pattern is generally constituted in the same direction or by a combination of two to three directions in a field. The light diffracted by the pattern is removed by a space filter disposed on the Fourier transformed plane in order to emphasize and detect only the light that is reflected by foreign matter.

There has further been proposed a method for detecting defects by comparing the data of an inspected reticle detected by using an optical system with the data of a standard reticle detected using said system or with design data, as disclosed, for example, in Japanese Patent Laid-Open No. 139278/1983.

According to Japanese Patent Laid-Open No. 65428/1984 that pertains to the prior art as described above, the light reflected by foreign matter is split by the shutter from the light reflected by the pattern, the light reflected by foreign matter is detected by the slit, and the foreign matter is detected by the binary method contributing to simplifying the detecting mechanism. However, the foreign matter is detected by an indirect illumination, i.e., illumination by laser beam from an upper tilted direction, which is different from the traditional exposure system. Namely, only the light reflected by the chrome pattern of a particular angle is shut off, and foreign matter is not discriminated relying upon the whole chrome pattern.

When foreign matter is detected by the indirect means as described above, even foreign matter having no real problem (hereinafter referred to as lie detecting) is detected. In particular, when the foreign matter increases with the decrease in the size of the patterns, the foreign matter that has problems increases, too, though the problems may not yet be regarded as real problems. Therefore, the number of lie detections increases, and an increased amount of work is required for checking, analyzing and removing foreign matter, detrimental to operation efficiency.

Next, Japanese Patent Laid-Open No. 139728/1983 that also pertains to the aforementioned prior art has an optical system similar to the exposure system, making it possible to simply constitute the optical system compared with that of the aforementioned prior art. However, the image signal processing system for comparing the data is complex compared with that of the aforementioned prior art and requires an extended period of time for inspection.

Furthermore, a variety of devices have been developed for detecting foreign matter adhered onto the reticles and masks. According to the prior art disclosed in Japanese Patent Laid-Open No. 65428/1984, the reticle is directly illuminated by a polarized laser at a predetermined angle of incidence, and the foreign matter is discriminated by utilizing the fact that the foreign matter has a direction of polarization in the reflected light different from those of the reticle substrate and the pattern. According to the prior art disclosed in Japanese Patent Laid-Open No. 101390/1984, attention is given to the fact that the pattern edge on the reticle is generally in the same direction or consists of a combination of two to three directions in the field. Further, the diffracted light caused by the pattern edge is removed by a space filter disposed on the Fourier transformed plane, to emphasize and detect only the light that is reflected by the foreign matter.

According to the prior apparatus disclosed in Japanese Patent Laid-Open No. 186324/1984, attention is given to the fact that the scattered light caused by the pattern edge has directivity but the scattered light caused by foreign matter has no directivity, and the foreign matter is discriminated relying upon the logical product of light quantities received by the light-receiving elements installed at a plurality of places.

According to the prior apparatuses disclosed in Japanese Patent Laid-Open Nos. 154634/1985 and 154635/1985, the foreign matter is discriminated by arranging a plurality of detectors utilizing the phenomenon in that the diffracted light caused by the pattern edge is focused in a predetermined direction only whereas the scattered light caused by foreign matter is scattered in all directions.

In the manufacture of semiconductor devices such as LSI's, a pattern on a master plate called reticle is printed by baking onto a semiconductor wafer in the step of exposure. In this case, if foreign matter exists on the reticle, the pattern is not correctly printed and all of the chips become defective. It is therefore necessary to detect foreign matter prior to effecting the baking from the standpoint of controlling the quality of reticles.

In producing the reticles and masks, however, the residue of resist, the remnants of chromium or chromium oxide for pattern formation after the etching, and impurities that are dissolved in the reticle wash liquid and that coagulate at the time of washing and drying the reticle, adhere onto the reticle. However, such foreign matters were so tiny and formed a thin contaminant film that there seldom arouse any problem thus far. As the technology for highly densely integrating the LSI's advances and as the wiring patterns become more fine, however, the presence of foreign matter of the order of submicrons becomes a serious problem though that was not so far regarded as a problem.

According to the conventional apparatus disclosed in Japanese Patent Laid-Open No. 65428/1979, however, the light reflected by tiny foreign particles and thin contaminant films is so weak compared with the light reflected by the pattern edge that it is not possible to distinguish the pattern edge over the tiny foreign particles and thin contaminant films. The light reflected by the tiny foreign particles can be emphasized utilizing the conventional technology disclosed in Japanese Patent Laid-Open No. 101390/1984. However, limitation is imposed on the light reflected by the pattern edge that can be erased, and it is impossible to remove all of the light reflected by the pattern edge using the same space filter.

According to any other prior technology, it is not allowed to distinguish tiny foreign particles of smaller than 1 μm and thin contaminant films over the pattern edges. This is because, the light is illuminated over a wide area according to the conventional art, and the sum of strength of the scattered light caused by the pattern edge so increases that the signals of scattered light caused by tiny foreign matter become undistinguishable. Even if the numerical aperture of the lens is increased in order to avoid such adverse effects, it is not allowed to distinguish the pattern edge over the foreign matter with the conventional apparatus. This is because, if the numerical aperture of the lens is great, the light is illuminated from many directions whereby the light scattered by the pattern edge loses directivity making it difficult to distinguish the light over the light scattered by foreign matter. That is, limitation is imposed on reducing the illuminated region based upon the method which illuminates one point.

SUMMARY OF THE INVENTION

A first object of the present invention is to provide a method and an apparatus for detecting abnormal patterns, which are free from the problems inherent in the aforementioned prior art, and which separate and detect only those foreign matters that have problem from a chrome pattern that exists maintaining a given angle.

A second object of the present invention is to provide a method and an apparatus for detecting abnormal patterns, which are capable of discriminating even those tiny foreign matters and thin contaminant films of the order of submicrons.

To achieve these objects, the present invention deals with a system for detecting abnormal patterns in a surface pattern on the surface of a sample, wherein when the abnormal pattern has a portion smaller than the surface pattern, the light for illuminating the sample is stopped down to an opening for distinguishing the abnormal pattern over the surface pattern, the surface pattern is limited by the illumination light to a predetermined opening to form an image on a detector, and the surface pattern detected by the detector is processed to detect the abnormal pattern in the surface pattern.

DESCRIPTION OF THE PREFERRED EMBODIMENTS

The action that corresponds to the first object of the present invention will now be described with reference to detecting tiny foreign matter and defects on the surface pattern on the reticle.

The present invention is based on the discovery that the flux of light that contributes to imaging undergoes the diffraction and scattering due to foreign matter and defects; i.e., based on the discovery that defective printing is caused by foreign matter and defects.

Generally, the numerical aperture (hereinafter referred to as N.A.) of the incident side (object side) of a reduction projection lens has been selected so as to provide sufficiently large resolving power for imaging a pattern on the reticle. Therefore, the flux of light that contributes to imaging the pattern passes through an opening on the incident side of the reduction projection lens, but the flux of light that passes through the outside of the opening does not contribute to imaging the pattern. When there exists tiny foreign matter, the flux of light scattered and diffracted by the foreign matter passes from the incident side N.A. to the outside of the reduction projection lens to impair the imaging of the pattern.

This point can be comprehended from the description of, for example, "Wave Optics", written by Hiroshi Kubota, pp. 387–389, "Response Function of an Optical System having Space Filter". That is, the above literature describes that when a disc-like space filter is set on a Fourier transformed plane of an imaging optical system and when the inside of, for example, a lens of a space frequency determined by the diameter of the disc-like space filter is covered by a circle having a diameter d', only the pattern having particular space frequency determined by the radius d' is not resolved. Therefore, this description can also be adapted to the technology for detecting foreign matter only by utilizing the difference in space frequency between the pattern and the foreign matter or, in other words, by utilizing the difference in size between the pattern and the foreign matter.

According to the present invention based upon the above-mentioned principle, use is made of an illumination system equivalent to the illumination system employed in the exposure system as well as an object lens having an N.A. larger than the N.A. of the reduction projection lens. As for the flux of light incident on the object lens, furthermore, the same region as the N.A. of the incident side of the rejection projection lens is shut off, i.e., the diffracted light is shut off by the shutter, in order to receive only the light scattered by foreign matter.

According to the present invention, therefore, only the flux of light that passes through an opening of the object lens is selectively detected, the flux of light being scattered and diffracted by foreign matter and defects and passing through the outside of opening of the incident side of the reduction projection lens. Therefore, those foreign matters having problem are enhanced and detected. And thus it is possible to distinguish those foreign matters among the patterns only by binarizing the detected signal. And even when comparing data of inspected reticle with those of standard, by the art as are disclosed e.g. in the Japanese Patent Laid-Open No. 139278/1983, S/N ratio of the signal of the foreign matters increases, since said signal of the foreign matters are enhanced.

The foregoing and other objects, advantages, manner of operation and novel features of the present invention will be understood from the following detailed description when read in connection with the accompanying drawing.

[First Embodiment]

A first embodiment of the present invention will now be described in conjunction with FIGS. 1 to 4.

Figure 1:
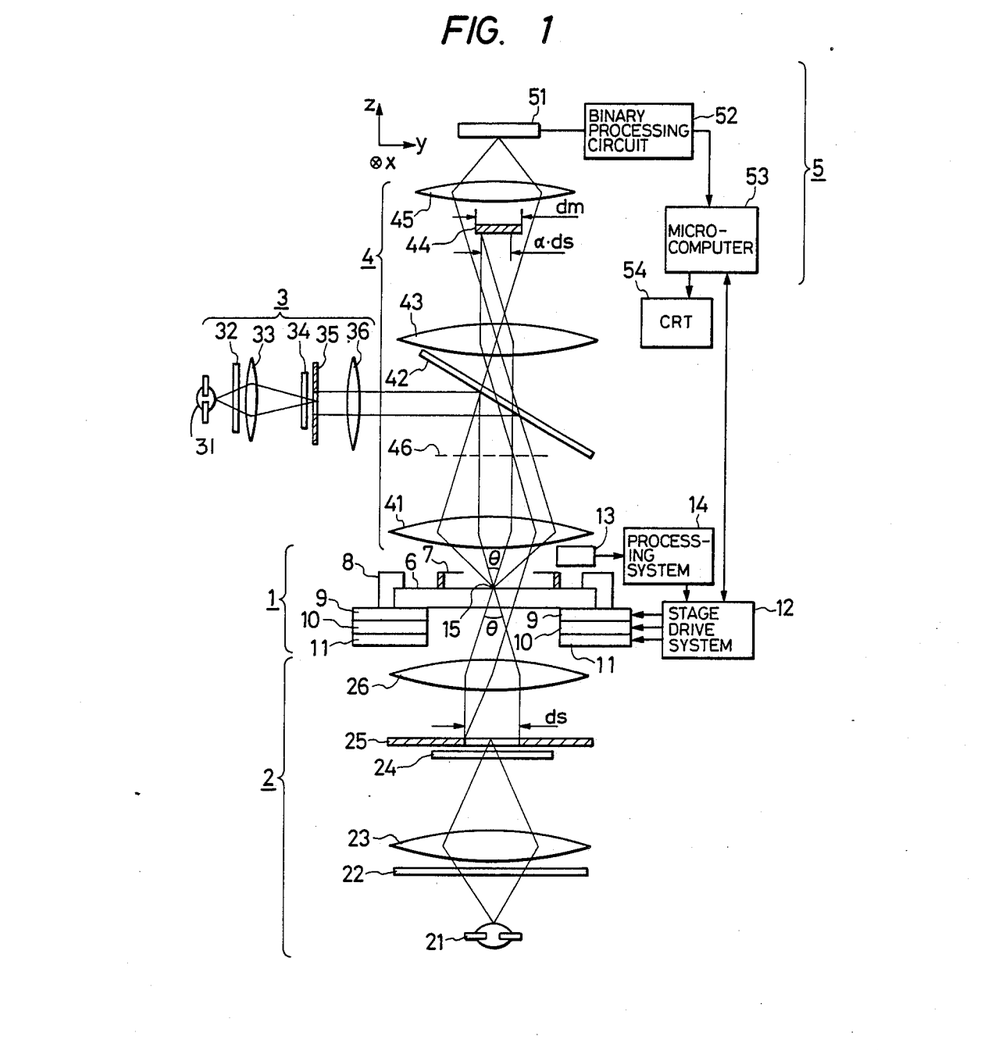
FIG. 1 is a block diagram of a foreign matter inspecting apparatus according to an embodiment of the present invention.

The foreign matter inspection apparatus according to the present invention consists, as shown in FIG. 1, of a sample stage system 1, a transmitting illumination sytem 2, a falling illumination sytem 3, a detection system 4, and a processing system 5.

The sample stage system 1 consists of a Zstage 9 which fastens thereto a reticle 6 having a pericle 7 by a fastening means 8 to scan it in the Z-direction, an X-stage 10 which scans the reticle 6 in the X-direction via the Z-stage 9, a Y-stage 11 which scans the reticle 6 in the Y-direction via the X-stage 10 and Z-stage 9, a stage drive system 12 for driving the stages 9, 10 and 11, a focal point position detect system 13 which detects the position of the reticle 6 in the Z-direction, and a processing system 14 for driving the stage drive system 12 in response to an instruction from the focal point position detect system 13. The sample stage system 1 accomplishes the focusing maintaining a required minimum precision while the reticle 6 is being inspected.

The X-stage 10 is designed to perform a periodical motion consisting of a time of uniform acceleration of about 0.1 second, a uniform motion of 0.1 second and a time of uniform deceleration of 0.1 second at a one-half period, at a maximum speed of about 1 mm/sec and an amplitude of 200 mm.

The Y-stage 11 is designed to move the reticle 6 in the Y-direction stepwisely by 0.15 mm each time in synchronism with the time of uniform acceleration and the time of uniform deceleration of the X-stage 10. If the recticle 6 is moved 670 times during the one time of inspection, the movement of 100 mm is accomplished in about 130 seconds. Namely, a square region having a side of 100 mm can be scanned in about 130 seconds.

The X- and Y-stages 10 and 11 are put into practice in this embodiment. However, the invention is in no way limited thereto only, but it is also allowable to use an X$\theta$-stage for effecting the scanning in the rotational direction and in the X-direction. Further, the aforementioned running speed is only an example which may be set to any value depending upon the requirement.

Further, the aforementioned focal point position detect system 13 may employ an air micrometer, or may detect the position relying upon the laser interference method, or may project a fringe pattern to detect the contrast.

The transmitting illumination system 2 is so constructed that a g-line (wavelength, 436 mm) or an i-line (wavelength, 365 mm) to be used in the exposure system (not diagrammed) is selected by a dichroic filter 22 from the flux of light emitted from a mercury lamp 21, the selected line is focused on a diffuser 24 by a focusing lens 23, the light diffused by the diffuser 24 is emitted through a portion that is limited by a circular opening to enter into a collimator lens 26, so that the reticle 6 is illumianted.

The opening 25 is positioned nearly at the position of focal point of the collimator lens 26, so that an image is formed at a position of focal point 46 indicated by a chain line above the collimator lens 26 and the object lens 41 of the detection system 4.

To achieve the above-mentioned object of the present invention, furthermore, it is necessary not only to set the wavelength of the illuminating light to be equal to the wavelength of the illuminating light used for the exposure system but also to maintain constant the angle $\theta$ of the flux of light incident on a point 15 on the reticle 6. Here, sin $\theta$ is defined to be "spatial coherency".

In the exposure system, furthermore, the whole area on the reticle 1 must be uniformly illuminated. For this purpose, therefore, use is made of an optical element called integrator which consists of a set of rod-like lenses instead of using the diffuser 24. The function of the integrator is basically the same as that of the diffuser 24. The range of inspection to which the present invention is applied is from several hundred of microns to 1.2 mm of the reticle 6. Therefore, the above-mentioned diffuser 24 suffices for the need.

Furthermore, since the angle of incidence $\theta$ of the flux of light incident on the reticle 6 is determined by the size of the integrator, i.e., by the diameter of opening 25 located at the back of the diffuser 24, the size of the opening 25 is so selected that the spatial coherency becomes the same as that of illumination employed for the exposure system that uses the reticle 1.

In the exposure system, the position of the integrator is not necessarily set to the position of focal point of the collimator lens 26, and the position of the opening 25 needs not necessarily be set to the position of focal point of the collimator lens 26.

To maintain the angle of incidence $\theta$ of the flux of light at a given position in a range illuminated with light on the reticle 6, however, it is desired that the opening 25 is located at the position of focal point of the collimator lens 26. This makes it possible to establish the same condition of illumination by the flux of light in a measuring range to detect foreign matter under the same condition.

The falling illumination system 3 is so constructed that the light emitted from a mercury lamp 31 is permitted to pass through a dichroic filter 32, a focusing lens 33, a diffuser 34 and an opening 35, and through a relay lens 36 to illuminate the reticle 6 via a half mirror 42 and the object lens 41 in the detection system.

The object lens 41 has the same function as the collimator lens 26 in the transmitting illumination system 2.

The relay lens 36 is provided to form an apparent opening at the position of focal point 46 over the object lens 41. Concretely speaking, a real image of the opening 35 is formed at the position of focal point 46.

Even in the falling illumination system 3, the opening 35 is so determined that the wavelength of the illuminating light and the angle $\theta$ of the light flux incident on a given point 15 on the reticle 6 will become the same as those of the illumination light used in the exposure system like in the aforementioned transmitting illumination system 2.

Furthermore, the falling illumination system 3 is provided to detect foreign matter on the chrome pattern on the reticle 6, but needs not be provided when there is no need of detecting foreign matter on the chrome pattern.

Moreover, when the falling illumination system 3 is to be used simultaneously with the transmitting illumination system 2, the signal from the edge of the pattern increases. When this becomes a problem, therefore, they must be separately used.

The wavelength of the illumination light needs not necessarily be limited to g-line and i-line only but may lie over a wide band that includes g-line and i-line. This is because, the diffraction condition of light differs over the whole wavelengths between the foreign matter and the pattern, and the foreign matter can be detected being distinguished over the pattern even with the light of a wide band.

The detection system 4 comprises an object lens 41, a half-mirror 42, a field lens 43, a shutter 44 and an imaging lens 45, so that the image at a point 15 of inspection on the reticle 6 is formed on a detector 51 through the object lens 41 and the imaging lens 45. The detection system further includes a field lens 43 near a position where the image is formed by the object lens 41. The field lens 43 forms the focal point position 46 on the upper side of the object lens 41 on the circular shutter 44. That is, the image of the opening 25 of the transmitting illumination system 2 passes through the collimator lens 26 and the object lens 41, reflected by the reticle 6, passes through the object lens 41 again, passes through the field lens 46, and is formed on the shutter 44. Here, the shutter 44 is located at a Fourier transformed position of the reticle 6 with respect to the position of the source of light, i.e., with respect to the position of the opening 25.

Generally, the N.A. of the reduction projection lens of the exposure system on the side of the reticle 6 has been set to be greater by 10 to 40% than the spatial coherency of the illumination system of the exposure system (which is equal to the spatial coherency of the transmitting illumination system 2). In many cases, the N.A. has been set to be greater by about 10%.

The flux of light that passes through the outside of the opening on the incident side of the reduction projection lens, must be caused to pass through the opening. For this purpose, the N.A. of the object lens 41 is set to be greater than the N.A. of the reduction projection lens. Furthermore, the shutter 44 is provided to shut off the flux of light that is incident on the N.A. of the reduction projection lens.

In order to achieve the object of the present invention, therefore, it is desired to calculate the diameter dm of the shutter 44 according to the following equation (1), i.e., $$dm = d_s \cdot \alpha \cdot \frac{N.A.}{\sin \theta_s} \cdot (1 + \delta) \tag{1}$$

where $d_s$ denotes the diameter of the opening 25, $\alpha$ denotes the magnification of the imaging system consisting of opening 25 and shutter 44, N.A. denotes a value of the reduction projection lens on the side of reticle 6, and $\sin \theta_s$ denotes the spatial coherency of the exposure system.

It was mentioned already that the conditions for detecting the foreign matter can be maintained constant if $\theta = \theta_s$. Symbol $\delta$ denotes a margin which, the experiment proves, may be several percent.

When all of the regions on the reticle 6 are to be simultaneously inspected, the object lens 41 becomes so bulky that that manufacture of it involves great difficulty. According to the present invention, therefore, the inspection region is limited on the reticle 6 which is scanned by the sample stage system 1 so that all of the regions can be inspected. It is therefore allowed to use the object lens 41 having N.A. greater than that of the reduction production lens which is usually used.

To detect foreign matter inclusive of those foreign matter that may not pose problem, the shutter 44 needs not necessarily be brought into conformity with the N.A. of the reduction projection lens of the incident side but may be brought into conformity with the spatial coherency of the transmitting illumination system 2 and the falling illumination system 3. That is, what is needed is to shut off the 0-th order diffraction light of illumination light from the transmitting illumination system 2 and the falling illumination system 3. Further, the size thereof may be greater than the above size. Concretely speaking, N.A./$\sin \theta$ is set to be 1 in the aforementioned equation (1), and δ is set to any value which is several percent or greater.

The spatial coherency of the illumination light needs not necessarily be brought into agreement with the coherency of the exposure system, but the sizes of the openings 25, 35 and the shutter 44 may be so determined that the θ-th order diffraction light is shut off by the shutter 44, i.e., that the aforementioned equation (1) is satisfied.

When the falling illumination system 3 is not provided, none of the half-mirror 42, field lens 43 and imaging lens 45 are needed, and the shutter 44 should be installed at the position of focal point 46 and the detector 51 should be installed at the position where the field lens 43 was located, to obtain the effects of the present invention. In this case, the optical system features a very simple construction.

The signal processing system 5 consists of detector 51, binary processing circuit 52, microcomputer 53 and CRT 54.

The detector 51 is comprised of, for example, a one-dimensional solid imaging device of the charge coupled type to detect signals while scanning on the X-stage 10. That is, when there exists foreign matter on the reticle 6, the level and the intensity of light increase and the output of the detector 51 increases.

The detector 51 needs not necessarily be comprised of the one-dimensional solid imaging element but may be comprised of the two-dimensional element, or of a single element.

The binary processing circuit 52 sets a binary threshold value in advance to determined the presence or absence of foreign matter.

The microcomputer 53 evaluates in advance the function of foreign matter that poses problem, since whether the printing is inhibited by the foreign matter or not is determined by the function of the strength of the scattered light caused by the foreign matter and the size of the foreign matter. The microcomputer 53 further determines the presence or absence of foreign matter that poses problem relying upon the evaluated function, and sends the result to the CRT 54.

The apparatus for inspecting foreign matter according to the present invention is constructed as described above. The method of inspection will now be described in conjunction with FIGS. 2 to 4.

Figure 2:
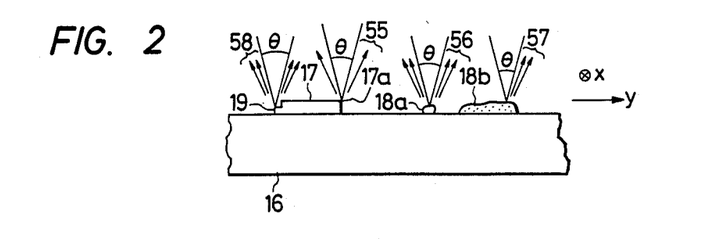
FIG. 2 is a diagram for explaining the scattering and diffraction caused by foreign matter on the sample and by defects in the pattern.

FIG. 2 illustrates the case where there exist a pattern 17, two foreign matters 18a, 18b and a defect 19 on a glass substrate 16. The smaller foreign matter 18a is so tiny that it causes the light to be more scattered or diffracted than by the edge 17a of the pattern 17. That is, the flux of light 56 scattered on the outside of the range θ shut off by the shutter 44 becomes greater than the flux of light 55 scattered by the edge 17a of the pattern 17.

Moreover, since the surrounding space frequency is high, the fluxes of light 57 and 58 scattered by the larger foreign matter 18b and the defect 19 of the pattern 17 on the outside of the range θ shut off by the shutter 44 become greater than the flux of light 55 scattered by the edge 17a of the pattern 17.

Figure 3:
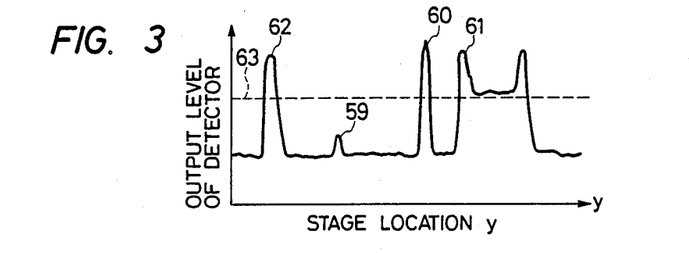
FIG. 3 is a diagram of output curves of a detector which detects foreign matter on the sample and defects in the pattern shown in FIG. 2.
Figure 4:
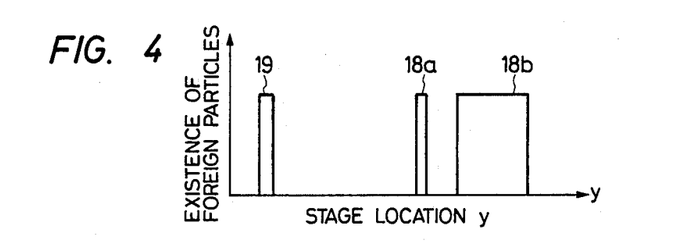
FIG. 4 is a diagram which shows the output signals shown in FIG. 3 in a binary form.

Therefore, the outputs of the detector 51 generate output peaks 59, 60, 61 and 62 due to the fluxes of light 55, 56, 57 and 58 as shown in FIG. 3.

Furthermore, a threshold value 63 is set by the binary processing circuit 52 as shown in FIG. 3. In this case, the three output peaks 60, 61 and 62 are greater than the threshold value 63, from which it is made possible to detect two foreign matters 18a, 18b and the defect 19 of pattern 17.

The coordinates of the X- and Y-stages 10 and 11, and the levels of the output peaks 60, 61 are stored in a memory that is controlled by the microcomputer 53, and the stored contents are processed and are produced to the CRT 54.

According to the present invention, use is made of illumination which is optically equivalent to the illumination of the exposure system, and the light is selectively detected which is scattered and diffracted by foreign matter and defects and which is no more incident on the reduction projection lens of the exposure system. Therefore, only those foreign matters that impose problem are detected being distinguished over the pattern.

Furthermore, the inspection region is limited on the reticle, and the reticle is scanned to inspect all of the regions. Therefore, there can be used an object lens having N.A. which is greater than that of the reduction projection lens that is usually used.

Moreover, the structure of the illumination system can be simplified, and employment of the binary processing circuit helps simplify the structure of the detection system.

[Second Embodiment]

The second embodiment comprises means for illuminating a plurality of light rays of good directivity on a point on the surface of a sample maintaining a predetermined angle of incidence from different directions, an optical detection system having a predetermined numerical perture for forming the image of light reflected by the sample, a light detector installed at the position where the image is formed, separation means which is illuminated by the plurality of said illumination means and which separate the light reflected by the surface of the sample or separate the detect signals of said light detector so that they are corresponded to the light rays, and means for processing the detect signals that are obtained through the separation.

In the above-mentioned optical detection system in which the angle of incidence of the plurality of light rays is all i and the number of light rays is m, it is recommended that lenses having the above-mentioned numerical aperture N.A. are arranged for the positions where the sources of illumination of the number m are arranged so as to satisfy the following relation, $$N.A. < \sin i \cdot \sin (\pi/2m) \quad (2)$$

Next, action of the second embodiment that corresponds to the second object of the present invention will be described.

According to this embodiment, the light having high directivity reflected by the pattern edge is almost all removed by a spatial filter defined by the plural sources of illumination and reflected light detect lenses that are arranged to satisfy the above relation (2). Moreover, since a laser beam having high directivity is used as illumination light, the region being illuminated increases and whereby it is allowed to use a lens of a large numerical aperture N.A. Therefore, the region to be detected can be squeezed to a tiny region. Concretely speaking, the region to be detected can be squeezed to a square region each side measuring from 0.5 μm to 3 μm, that is suited for detecting foreign matter of 0.1 μm in size. Moreover, the embodiment is of the type which is illuminated from many directions but which detects in one direction only. Therefore, the light reflected by the pattern edge may not be detected when it is illuminated by the source of illumination of some directions. On the other hand, the foreign matter scatters the light from all sources of illumination. Therefore, by separating the reflected light or detect signals to correspond to the sources of illumination and by finding a logical product thereof, it is made possible to discriminate tiny foreign matter and thin contaminant films from the pattern edges.

The second embodiment of the present invention will now be described in conjunction with the drawings.

Figure 5:
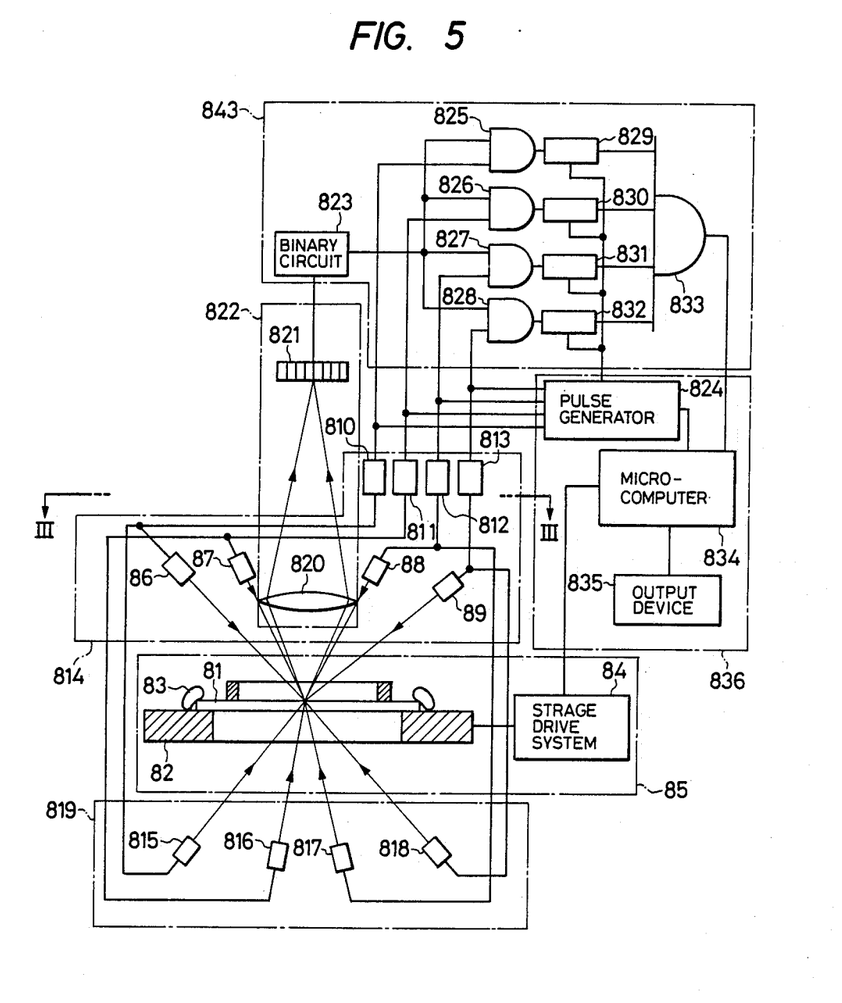
FIG. 5 is a diagram illustrating the structure of an apparatus for discriminating a pattern and foreign matter according to a second embodiment of the present invention.

FIG. 5 is a diagram illustrating the structure of a pattern/foreign matter discriminating apparatus according to the second embodiment of the present invention. The pattern/foreign matter discriminating apparatus of this embodiment consists of a stage system 85 for placing a sample 81 to be inspected such as reticle, a reflection illumination system 814, a transmitting illumination system 819, a detection system 822, a signal processing system 843, and a control system 836.

The stage system 85 consists of a stage 82 on which will be placed the sample 81 to be inspected, a clamp 83 for mechanically fastening the sample 81 to be inspected to the stage 82, and a stage drive system 84 for driving the stage 82 in the X-direction and Y-direction upon designation from a microcomputer 834 that will be described later.

The stage 82 performs a periodical motion consisting of a uniform acceleration motion of 0.1 second, a uniform motion of 0.1 second and a uniform deceleration motion of 0.1 second in, for example, the X-direction, at a one-half period at a maximum speed of about 1 m/sec and an amplitude of 200 mm. The stage 82 is further stepwisely sent by 0.15 mm each time in the Y-direction in synchronism with the time of uniform acceleration and the time of uniform deceleration in the X-direction. If the stage 82 is moved 670 times during one time of inspection, the movement of 100 mm is accomplished in about 130 seconds. Namely, a square region having a side of 100 mm can be scanned in about 130 seconds.

Figure 6:
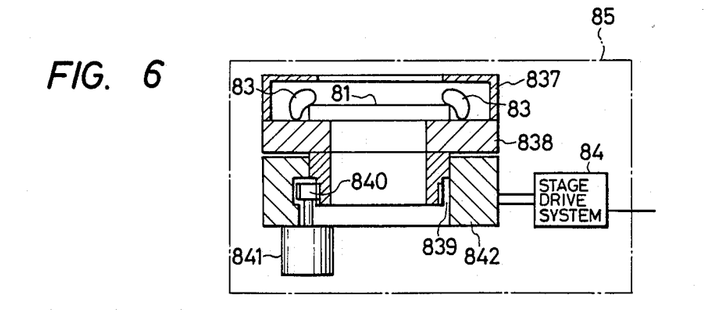
FIG. 6 is a diagram illustrating the structure of a stage according to a different embodiment.

Here, the stage 82 is in no way limited to the XY-stage of this embodiment only. For instance, it is allowed to use an $X\theta$-stage that is shown in FIG. 6. The $X\theta$-stage shown in FIG. 6 consists of an X-stage 842, an X-stage drive system 84, a $\theta$-stage 838, a $\theta$-stage drive system 841 for turning a gear 840 that meshes with teeth 839 formed on the periphery at the bottom of the $\theta$-stage 838, a mask 837 for covering the sample 81 to be inspected, and a clamp 83. For instance, the $\theta$-stage 839 turns at a constant speed four times a second, and the X-stage 842 is moved at a constant speed of $\theta$0.6 mm/sec by about 70 mm. Therefore, the square region with a side of 100 mm is scanned in about 120 seconds. In this case, the mask 837 fastened to the $\theta$-stage 838 prevents the light from falling on the regions except the region to be inspected.

The transmitting illumination system 819 of FIG. 5 consists of four laser diodes 815, 816, 817 and 818 that have a high-speed switching function and that are arranged under the sample 81 to be inspected and being tilted with respect to the sample 81 to be inspected.

The reflection illumination system 814 consists of four laser diodes 86, 87, 88 and 89 that have a high-speed switching function and that are arranged over the sample 81 to be inspected and being tilted with respect to the sample 81 to be inspected, and laser diode drive sources 810, 811, 812 and 813 for supplying drive pulse power to the laser diodes 86, 87, 88 and 89. The laser diode drive sources 810, 811, 812 and 813 are further connected to the laser diodes 815, 816, 817 and 818 in the transmitting illumination system 819, so that the laser beams are simultaneously emitted from the pairs of laser diodes 86 and 815, 87 and 816, 88 and 817, and 89 and 818.

Figure 7:
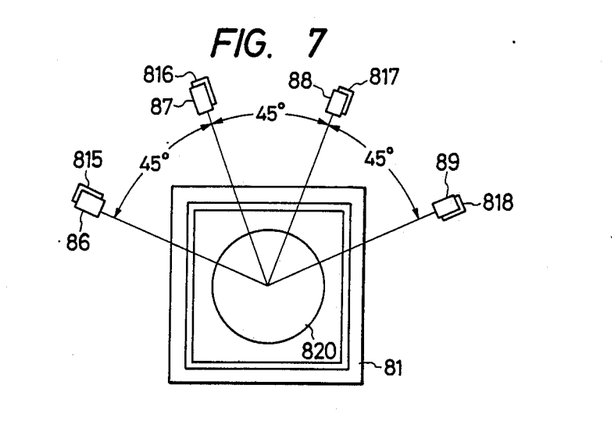
FIG. 7 is a section view along the line III—III of FIG.

The four laser diodes 86 to 89 in the reflection illumination system 814 and the four laser diodes 815 to 818 in the transmitting illumination system 819 are arranged at symmetrical positions with respect to the sample 81 to be inspected. These eight laser diodes emits laser beams onto a point on the sample 81 to be inspected at an angle of incidence i of 60°. FIG. 7 is a section view along the line III—III of FIG. 5. The four laser diodes 86 to 89 are so secured that their planes of incidence define an angle of 45° relative to the planes of incidence of the neighboring laser diodes.

The detection system 822 is constituted by an object lens 820 disposed just over the sample 81 to be inspected, and a detector 821 which consists, for example, of a one-dimensional pin silicon photodiode array that converts the image formed by the object lens 820 into an electric signal. The numerical aperture N.A. of the object lens 820 is so set as to satisfy the following equation (2), $$\text{N.A.} < \sin i \cdot \sin (\pi/2m) \qquad (2)$$

The object lens 820 may be comprised of a lens that satisfies the equation (2), or the numerical aperture N.A. may be varied by the opening to satisfy the equation (2). Here, symbol denotes an angle of incidence of the laser diodes 86 to 89, and m denotes the number of the laser diodes 86 to 89. That is, in this embodiment, $i=60°$ and $m=4$ and, hence, the numerical aperture N.A. of the lens is 0.33. In the equation (2), $(\pi/m)$ represents an angle 45° of the planes of incidence of the neighboring laser diodes.

The control system 836 consists of a pulse (timing) generator 824, a microcomputer 834, and an output device 835. The pulse generator 824 sends control pulses to the laser diode drive sources 810, 811, 812 and 813 successively upon designation from the microcomputer 834, so that the light is emitted from the laser diodes (86 and 815) → (87 and 816) → (88 and 817) → (89 and 818) in this order. The pulse generator 824 further sends pulses that are in synchronism therewith to the delay circuits (shift registers) 829 to 832 in the signal processing system 843 to oeprate them.

The signal processing system 843 is provided for each of the pixels of the detector 821 (FIG. 5 illustrates only one signal processing system), and is comprised of a binary circuit 823 for converting the detect signal of the detector 821 into a binary value, four two-input AND circuits 825, 826, 827 and 828 which receive output signal of the binary circuit 823 and pulse signals that are supplied from the pulse generator 824 to the laser diode drive sources 810 to 813, a four-stage shift register 829 for delaying the output signal of the AND circuit 825, a three-stage shift register 830 for delaying the output signal of the AND circuit 826, a two-stage shift register 831 for delaying the output signal of the AND circuit 827, a one-stage shift register 832 for delaying the output signal of the AND circuit 828, and a four-input AND circuit 833 which obtains a logical product of the output signals of these four shift registers 829 to 832 and which sends the result to the microcomputer 834. Thus, since there are provided shift registers 829 to 832 having numbers of delay stages that are varied by one relative to each other, the results obtained by illuminating the sample 1 to be inspected by a laser beam four times are sent to the AND circuit 833.

The microcomputer 834 receives a signal sent from the AND circuit 833 of the signal processing system 843 in synchronism with the drive control signal to the stage drive system 84. When there exists foreign matter, i.e., when the output of the AND circuit 833 assumes the high level, the microcomputer 834 stores the coordinate position of the stage 82 and sends the result of inspection to the output devices such as printer and display unit.

Described below is the operation of the pattern/foreign matter discriminating apparatus which is constructed as described above.

The sample 81 to be inspected is placed on the stage 82, and the pulse generator 824 is operated by a control signal from the microcomputer 834. First, the laser diodes 86 and 815 emit pulses of light for about 100 nanoseconds at a first timing. The light focused by the lens 820 when the laser beam is illuminated is converted into an electric signal by the detector 821. This signal is converted into a binary value by the binary circuit 823, and is sent to the four-stage shift register 829 via AND circuit 825.

After about 100 nanoseconds from the termination of the first pulse light, the laser diodes 87 and 816 emit pulses of light for about 100 nanoseconds at a second timing, and the detect signal is sent to the three-stage shift register 830. At the second timing, furthermore, the data stored in the four-stage shift register 829 is shifted by one stage.

After about 100 nanoseconds from the termination of the second pulse light, the laser diodes 88 and 817 emit pulses of light for about 100 nanoseconds at a third timing, and the detect signal is received by the two-stage shift register 831. At the third timing, furthermore, the data stored in the four-stage shift register 829 and in the three-stage shift register 830 are shifted by one stage.

After about 100 nanoseconds from the termination of the third pulse light, the laser diodes 89 and 818 emit pulses of light for about 100 nanoseconds at a fourth timing, and the detect signal is received by the one-stage shift register 832. At the fourth timing, furthermore, the data stored in the four-stage shift register 829, in the three-stage shift register 830 and in the two-stage shift register 831 are shifted by one stage.

At the next timing, the data in the shift registers 829 to 832 are simultaneously input to the AND circuit 833 which then sends an output signal to the microcomputer 834. The stage 2 is moved by a control signal from the microcomputer 834, and the aforementioned procedure is repeated in the next region of inspection.

How tiny foreign matter is detected by the above detect operation will now be described in conjunction with FIGS. 8 to 14.

Figure 8:
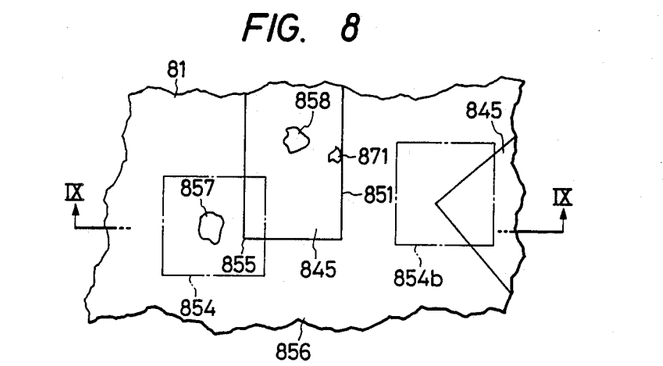
FIG. 8 is a view illustrating on an enlarged scale the surface of a sample that is to be inspected.
Figure 9:
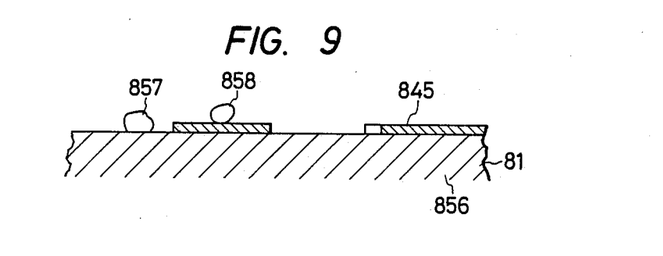
FIG. 9 is a section view along the line V—V of FIG. 8.

FIGS. 8 and 9 are a partial plan view and a partial section view of the sample that is to be inspected, and wherein reference numeral 856 denotes a glass substrate, 81 denotes a sample to be insepcted such as reticle or the like, 845 denotes a pattern, reference numerals 854 and 854b denote regions to be inspected, 857 denotes tiny foreign matter which is not placed on the pattern, 858 denotes foreign matter on the pattern, 871 denotes a pattern defect, 851 denotes a pattern edge, and 855 denotes a pattern corner.

Figure 10:
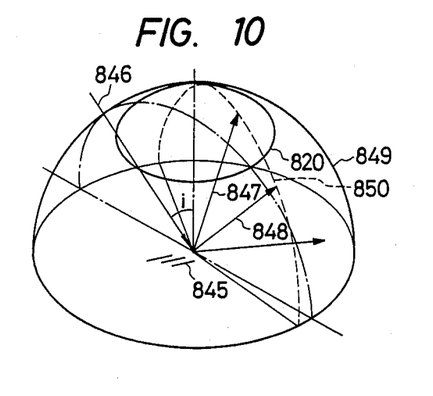
FIG. 10 is a diagram for explaining the diffraction phenomenon of light.
Figure 11:
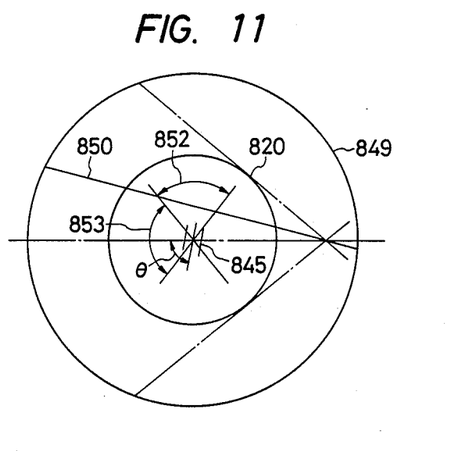
FIGS. 11 and 12 are a plan view and a side view of FIG. 10, respectively.
Figure 12:
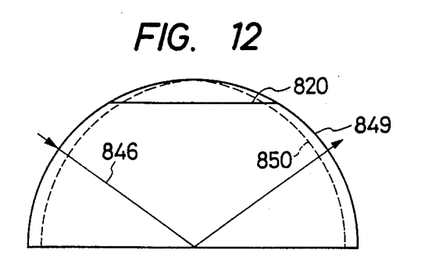

FIG. 10 is a diagram for explaining a general diffraction phenomenon. A flux of light 846 incident on the pattern 845 at an angle of incidence i is diffracted by the pattern edge to form fluxes of light 847 and 848. In FIG. 10, a spherical surface 849 in contact with the lens 820 is brought into consideration, to observe an intersecting point between the spherical surface 849 and the fluxes of light 846 to 848. FIG. 11 and 12 are a plan view and a side view of FIG. 10. A curve connecting the fluxes of diffracted light 847 and 848 describes a circle 850 as shown in FIG. 12 according to the theory of diffraction. The circle becomes a straight line in FIG. 11. That is, the diffracted light caused by the edge of the pattern 845 travels in the direction of circle 850. Here, the pattern 845 and the circle 850 are perpendicular to each other.

Figure 13:
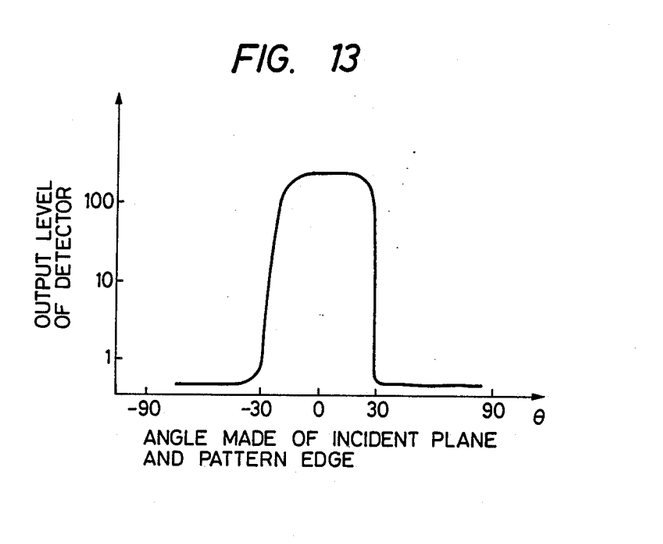
FIG. 13 is a graph that illustrates a relationship between the pattern edge angle and the intensity of the detected signal.

Therefore, when the direction of edge 851 of the pattern 845 is in a range 852 shown in FIG. 11, the diffracted lens enters into the lens 820. The diffracted light, however, does not enter into the lens 820 when the direction of edge 851 is in the range 853. This has been confirmed by experiment. FIG. 13 is a graph showing a relationship between the intensity of detect signals of the detector 821 from the pattern edge 851 and the angle between the direction of edge 851 and the plane of incidence when the numerical aperture N.A. of the lens 820 is 0.5 and i=60°. As will be obvious from this graph, the detect signals in a range $-30° < \theta < +30°$ have an intensity which is 500 times as great as the intensity of detect signals in other ranges.

That is, the diffracted light from the pattern edge enters into the lens 820 having the numerical aperture N.A. only when the following condition of the equation (3) holds true, i.e., $$N.A. > \sin i \cdot \cos \theta \tag{3}$$

In the case of FIG. 8, therefore, since there exists no pattern edge in the inspection field 854 that satisfies the equation (3), only the light that is scattered by the foreign matter 857 enteres into the lens 820, and the foreign matter 857 only is detected. When the inspection field is as denoted by 854b, on the other hand, the pattern edge is detected. According to this embodiment which is based upon the system of illumination in multi-directions and inspection in one direction, however, the pattern edge is not erroneously detected as foreign matter even when the inspection field is as denoted by 854b. This is explained below in conjunction with FIG. 14.

Figure 14:
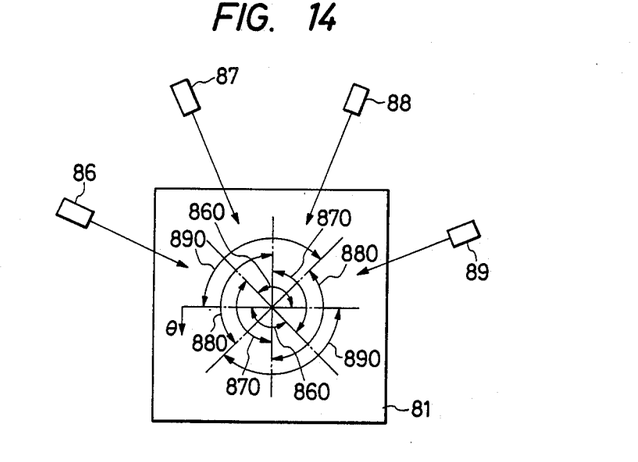
FIG. 14 is a diagram illustrating a relationship between the positions of four laser diodes and the pattern edge directions detected by the light emitted therefrom according to the second embodiment.

FIG. 14 illustrates a relationship between the pattern edge angle $\theta$ and the laser diode with which the pattern edge can be detected when the light is emitted. When the laser diode 86 emits light, there is detected a pattern edge whose edge angle $\theta$ lies within a range 860. When the laser diode 87 emits light, there is detected a pattern edge whose edge angle $\theta$ lies within a range 870. When the laser diode 88 emits light, there is detected a pattern edge whose edge angle $\theta$ lies within a range 880, and when the laser diode 89 emits light, there is detected pattern whose edge angle $\theta$ lies within a range 890. As will be obvious from FIG. 14, however, the pattern edge of any angle $\theta$ is not always detected whenever the light is emitted from the laser diodes 86 to 89. Therefore, if the logic product is found through the AND circuit 833, the pattern edge is not erroneously detected as foreign matter. Next, attention is given to a corner portion 855 where the two pattern edges intersect with each other. The corner portion can be regarded to be a set of various edges whose directions gradually change from 0° to 90°. Namely, since the angle θ of edge lies from 0° to 90°, any one of the four laser diodes necessarily fails to produce brightness. In the same manner as described above, therefore, this is not erroneously detected as foreign matter. In the case of this embodiment which employs four laser diodes 86 to 89, if the pattern corner that can be regarded to vary over a wide range of from 0 to 135 lies within an inspection field, the corner is brightened by the light emitted from all laser diodes and is detected like the foreign matter. In practice, however, the patterns usually used for the process for manufacturing the semiconductor devices contain such a particular pattern corner very little. Even if the corner is erroneously detected as foreign matter, therefore, there does not arise any serious problem.

Figure 15:
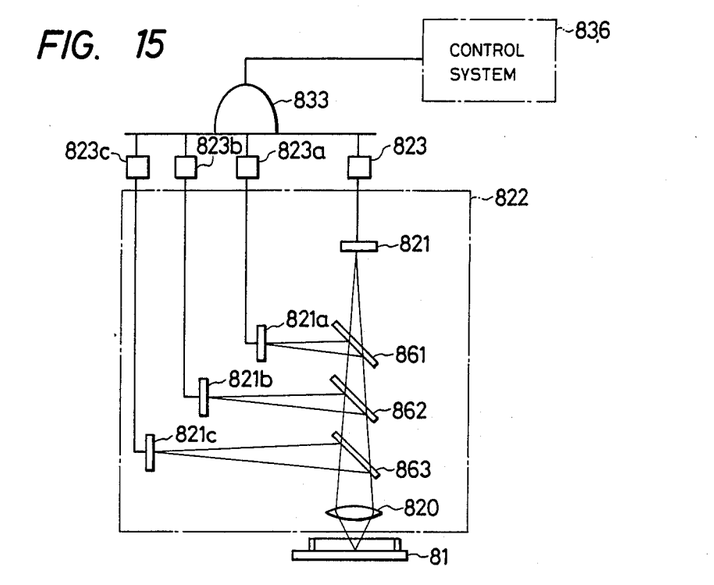
FIGS. 15 and 16 are diagrams illustrating the structure of detect signal separation means of the apparatus for discriminating patterns and foreign matter according to the second embodiment of the present invention.

As will be obvious from the above description, the direction of pattern edge varies from 0° to 180° with the increase in the inspection field, making it difficult to discriminate the pattern edge over the foreign matter. According to this embodiment, however, there is employed the system of illumination by laser beams in multi-direction and inspection in one direction, and the numerical aperture N.A. of the object lens is set to satisfy the equation (2). It is therefore allowed to select the inspection field to be narrower than the size of the pattern, and the pattern edge is not erroneously detected as foreign matter. Moreover, if there exists a pattern defect 871 in a narrow inspection field as shown in FIG. 8, the pattern defect 871 can be regarded to be a set of edges that varies from 0° to 180°, and can hence be detected in the same manner as the foreign matter. Unlike the light scattered by foreign matter, furthermore, the light diffracted by pattern edge is very little incident upon the object lens in compliance with the diffraction phenomenon. Utilization of this phenomenon makes it possible to discriminate tiny foreign matter and thin contaminant films maintaining a very high discrimination ratio compared with the method which is based on the polarization. The detect signal produced by foreign matter 857 on the glass substrate 856 is smaller than the detect signal produced by foreign matter 858 on the pattern 845 of the sample 81 to be inspected. In this embodiment provided with the transmitting illumination system 819, however, the detect signal by the foreign matter 857 becomes nearly equal to the detect signal by the foreign matter 858, and the detection never results in failure. In this embodiment, furthermore, the laser diodes are operated in a switching manner. It is, however, also allowable to turn the continuously oscillating laser on and off using the shutter With the pattern/foreign matter discriminating apparatus according to the aforementioned second embodiment, the detect signals are separated to correspond to the laser diodes For this purpose, therefore, the laser diodes are operated in a switching manner. However, the detect signals may be separated to correspond to the laser diodes by any other means. FIG. 15 is a diagram which illustrates the structure of signal separation means in the pattern/foreign matter discriminating apparatus according to a third embbdiment of the present invention. In this embodiment, use is made of laser diodes that produce laser beams of different wavelengths in place of the laser diodes 86, 815, 87, 816, 88, 817, 89 and 818 of the second embodiment. Further, mirrors 861, 862 and 863 for separating waveforms are installed at the back of the object lens 820. The detect light that has passed through the mirrors 861 to 863 and the detect light separated by mirrors 861 to 863 are converted into electric signals through the detectors 821, 821a, 821b, and 821c. The electric signals are then converted into binary values through binary circuits 823, 823a, 823b and 823c, and a logical product thereof is obtained through an AND circuit 833. The above structure makes it possible to obtain the same effects as those of the second embodiment.

Figure 16:
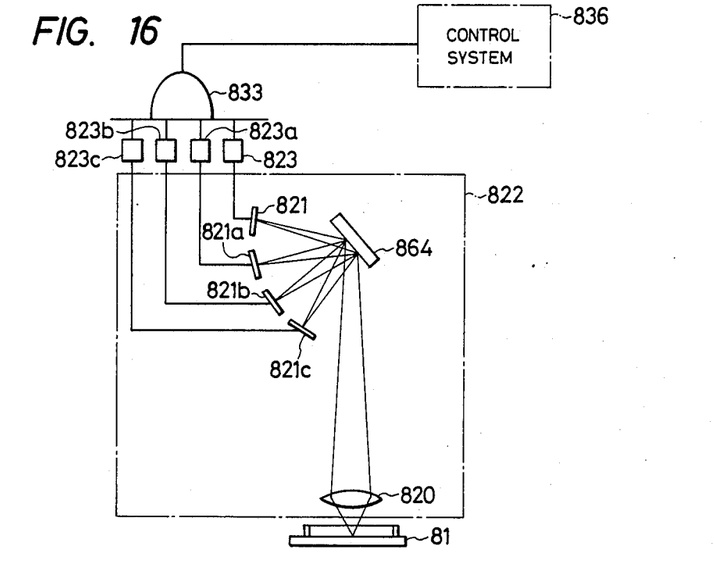

FIG. 16 illustrates an embodiment modified from the third embodiment of the present invetnion. In this case, the light of dissimilar wavelengths is separated by a diffraction grating 864, and the processing is effected by the detectors 821 to 821c in the same manner as that of the third embodiment.

The pattern/foreign matter discriminating apparatus of the present invention is constructed by making reference to the schlieren method and the principle of the phase contrast microscope. As a reference literature related thereto, there can be quoted, for example, "APPLIED OPTICS", by Hiroshi Kubota, pp 129–136 (Iwanami Zensho Co.). The diffraction phenomenon has also been mentioned on pp. 106–145 of this literature. As a reference literature related to the scattering phenomenon, there can be quoted "PRINCIPLES OF OPTICS" by Born and Woh, pp. 627–664.

According to the present invention, even those tiny foreign matter and thin contaminant films can be detected being distinguished over the pattern edge.

What is claimed is:

1. A method of detecting an abnormal pattern on an object body comprising the steps of:
   emitting an exposure light having a substantially single wave length;
   converting said exposure light into a diffused light with a first aperture;
   focusing said diffused light onto said object body with a specified spatial coherency for substantially preventing generation of scattered light by an edge of a pattern on said object body;
   imaging scattered light which is generated by a foreign particle on said object body;
   shielding with a shielding means substantially all scattered light generated by said edge of the pattern while passing outside thereof a component of said scattered light generated by said foreign particle when a spatial frequency of said foreign particle is higher than that of said edge of the pattern, said shielding means being disposed at a Fourier Transformed position of said object body with respect to said first aperture and having a second aperture which is slightly greater than said first aperture; and
   detecting an image of said component of said scattered light generated by said foreign particle, thereby detecting said foreign particle without detecting said edge of the pattern.

2. A method of detecting abnormal patterns according to claim 1, further comprising:
   adjusting said spatial coherency to a value nearly equal to a spatial coherency of an illumination means that is used for printing a pattern on said object body.

3. A method of detecting abnormal patterns according to claim 1, wherein said detecting step converts the detected image into binary values.

4. A method of detecting abnormal patterns according to claim 2, wherein said imaging step is performed using an object lens with a numerical aperture greater than the numerical aperture of an imaging means used for printing.

5. An apparatus for detecting an abnormal pattern on an object body comprising:
- a light source for emitting an exposure light having a substantially single wave length;
- diffusing means for converting said exposure light into a diffused light with a first aperture;
- a collimator lens for focusing said diffused light onto said object body with a specified spatial coherency for substantially preventing generation of scattered light by an edge of a pattern on said object body;
- an imaging lens system for imaging scattered light generated by a foreign particle on said object body;
- shielding means for substantially shielding all scattered light generated by said edge of the pattern while passing outside thereof a component of said scattered light generated by said foreign particle when a spatial frequency of said foreign particle is higher than that of said edge of the pattern, said shielding means being disposed at a Fourier Transformed position of said object body with respect to said first aperture and having a second aperture which is slightly greater than said first aperture; and
- detecting means for detecting an image of said component of said scattered light generated by said foreign particle, thereby detecting said foreign particle without detecting said edge of the pattern.

6. An apparatus for detecting abnormal patterns according to claim 5, which further comprises means for placing said object body in a position so that it can be scanned, and means for adjusting said spatial coherency.

7. An apparatus for detecting abnormal patterns according to claim 5, wherein said detecting means converts the detected image into binary values.

8. An apparatus for detecting abnormal patterns according to claim 5, wherein said imaging lens system has an opening greater tan that of an imaging means used for printing said pattern.

9. An apparatus for detecting abnormal patterns according to claim 5, wherein said diffusing means comprises a diaphragm for limiting said diffused light to said first aperture.

10. An apparatus for detecting abnormal patterns according to claim 5, wherein said specified spatial coherency substantially satisfies a relation of sin $\theta = ds/2f$, wherein $\theta$ is defined as an angular aperture, ds is a diameter of said first aperture when it is a circle, and f is a focal distance of said collimator lens.

11. An apparatus for detecting abnormal patterns according to claim 5, wherein said light source comprises a mercury lamp and said apparatus further comprises filter means for selecting said exposure light from a light emitted from said mercury lamp.

12. An apparatus for detecting abnormal patterns according to claim 5, further comprising:
- a second light source for emitting a second exposure light having a substantially single wave length;
- a second diffusing means for converting said second exposure light into a diffused light with a third aperture;
- a second collimator lens for focusing said light diffused by said first diffusing means on said object body with a predetermined spatial coherency for stopping the generation of scattered light by an edge of an abnormal pattern on said object body.

13. An apparatus for detecting an abnormal pattern according to claim 5, wherein said object body comprises a reticle.

14. An apparatus for detecting an abnormal pattern on an object body comprising:
- at least four laser diodes for respectively illuminating at least four coherent laser beams onto a point on said object body from directions which are inclined at a predetermined angle to a vertical optical axis and are spaced apart at intervals defined as a quotient of 180° divided by a predetermined value with said intervals being with respect to a horizontal plane;
- an optical system having an object lens which is used for forming respective images of scattered light generated by the illumination of said point by each of said at least four laser beams, said object lens further has a specific numerical aperture and is disposed so that scattered light generated by an edge of said abnormal pattern which is illuminated by at least one of said laser beam does not enter said object lens while scattered light generated by a foreign particle located at said point enters said object lens when said foreign particle has a predetermined size;
- means for separately detecting each of said respective images of scattered light and producing a plurality of signals indicated thereof; and
- means for determining the presence of an abnormal pattern on said object body based upon said separately detected images and producing a signal indicative thereof.

15. An apparatus for detecting abnormal patterns according to claim 14, wherein said object lens has a numerical aperture N.A. which satisfies the following relationship,
N.A. $< \sin i \cdot \sin(\pi/2m)$
where angles of incidence of said at least four laser beams are all i and the number of laser beams is m.

16. An apparatus for detecting abnormal patterns according to claim 14, wherein said determining means obtains a logical product of said plurality of signals indicative of said detected images.

17. An apparatus for detecting abnormal patterns according to claim 14, which further comprises means for pulsing said at least four laser beams at different times, and said means for separately detecting said respective images operates in synchronism with said means for pulsing.

18. An apparatus for detecting abnormal patterns according to claim 14, wherein said at least four laser beams have wavelengths that are different from each other, and said means for separately detecting said respective images separates the detected images depending upon their wavelengths.

19. An apparatus for detecting abnormal patterns according to claim 18, wherein said means for separately detecting said respective images comprises a wavelength separating mirror.

20. A method for detecting an abnormal pattern on an object body comprising:
- illuminating at least four coherent laser beams onto a point on said object body from directions which are inclined at a predetermined angle to a vertical optical axis and are spaced apart at intervals defined as a quotient of 180° divided by a predetermined value;

forming respective images of scattered light generated by illumination of said point by said at least four laser beams using an optical system with an object lens having a specific numerical aperture and which is disposed so that scattered light generated by an edge of sad abnormal pattern which is illuminated by at least one of said laser beams does not enter said object lens while scattered light generated by a foreign particle located at said point enters said object lens when said foreign particle has a predetermined size;

separately detecting each of said respective images of scattered light and providing a plurality of signals indicative thereof; and determining the presence of an abnormal pattern on said object body based on said plurality of signals.

21. A method of detecting abnormal patterns according to claim 20, wherein the determining step further comprises obtaining a logical product of said plurality of signals indicative of said respective images.

22. A method of detecting abnormal patterns according to claim 20, which further comprises a step for generating said at least four laser beams in the form of pulses at different times, and said step for separately detecting said respective images is performed in synchronism with the pulses.

23. A method of detecting abnormal patterns according to claim 20, wherein said at least four laser beams have wavelengths that are different from each other, and said step for separately detecting said respective images further comprises separating the detected images depending upon their wavelengths.

24. A method of detecting abnormal patterns according to claim 20, wherein said step of forming images is performed by an optical system having a lens with a numerical aperture aperture N.A satisfying the following relationship, $$N.A. < \sin i \cdot \sin(\pi/2m)$$

where angles of incidence of said at least four laser beams are all i and the number of laser beams is m.

* * * * *